United States Patent
Hasegawa et al.

(12)
(10) Patent No.: US 6,295,368 B1
(45) Date of Patent: Sep. 25, 2001

(54) ENDOSCOPIC IMAGE PROCESSING SYSTEM CAPABLE OF ESTIMATING ABSOLUTE SHAPE OF OBJECT ENTITY

(75) Inventors: Jun Hasegawa; Tetsuo Nonami, both of Hino (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 09/288,492

(22) Filed: Apr. 8, 1999

(30) Foreign Application Priority Data

Apr. 10, 1998 (JP) .................................................. 10-099516

(51) Int. Cl.⁷ ........................................................ G06K 9/00
(52) U.S. Cl. ............................................................. 382/128
(58) Field of Search ..................................... 382/128, 130, 382/131, 132, 154, 203, 206, 276, 285, 286, 291, 294, 305; 606/32, 33, 34, 46, 47, 48; 348/45, 65, 72

(56) References Cited

U.S. PATENT DOCUMENTS

| 4,962,540 | 10/1990 | Tsujiuchi et al. | 382/165 |
| 5,432,543 | * 7/1995 | Hasegawa et al. | 348/45 |
| 5,833,608 | * 11/1998 | Acker | 600/409 |
| 6,016,439 | * 1/2000 | Acker | 600/411 |

FOREIGN PATENT DOCUMENTS

| 6055479 | 3/1985 | (JP) | G02B/23/24 |
| 63240831 | 10/1988 | (JP) | A61B/5/10 |
| 63244011 | 10/1988 | (JP) | G02B/23/24 |
| 63246716 | 10/1988 | (JP) | G02B/23/24 |
| 06007289 | 1/1994 | (JP) | A16B/1/04 |
| 9026547 | 1/1997 | (JP) | G02B/23/24 |
| 9140665 | 6/1997 | (JP) | A61B/1/04 |

OTHER PUBLICATIONS

"A Primer of Computer Image Processing" under the supervision of Hideyuki Tamura, pp. 148–151.

* cited by examiner

Primary Examiner—Andrew W. Johns
Assistant Examiner—Shervin Nakhjavan
(74) Attorney, Agent, or Firm—Ostrolenk, Faber, Gerb & Soffen, LLP

(57) ABSTRACT

An endoscopic system comprises an endoscope system, an endoscopic position detecting apparatus, and an image processing apparatus. The endoscope system enables endoscopic examinations. The endoscopic position detecting apparatus detects the three-dimensional positions of the distal part of the endoscope in a body cavity. The image processing apparatus estimates the shape of an object entity visualized by the endoscope. The image processing apparatus is used as a means for grasping the shape of an object entity in a body cavity. For this purpose, the insertion unit of an electronic endoscope is inserted into the body cavity of a patient lying down on a patient couch. Specifically, a main unit of the image processing apparatus is connected to a video processor over a cable, and receives an image signal (R, G, and B signals and a sync signal) sent from the video processor. The main unit of the image processing apparatus estimates relative shapes according to successive image signals representing the object entity and being sent from the video processor. The main unit of the image processing apparatus then calculates the absolute shape of the object entity according to the position data of the distal part of the electronic endoscope sent from a main unit of the endoscopic position detecting apparatus.

18 Claims, 10 Drawing Sheets

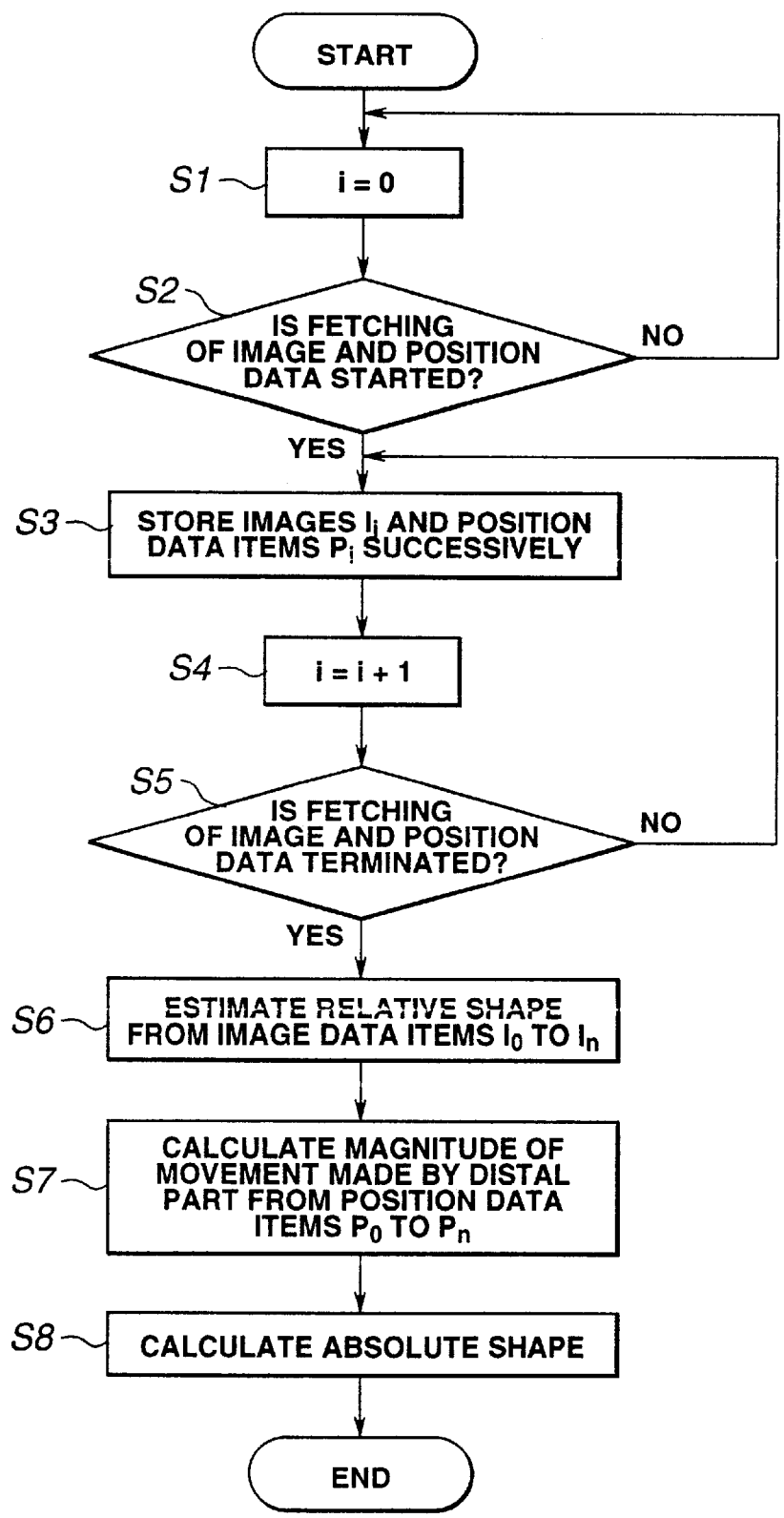

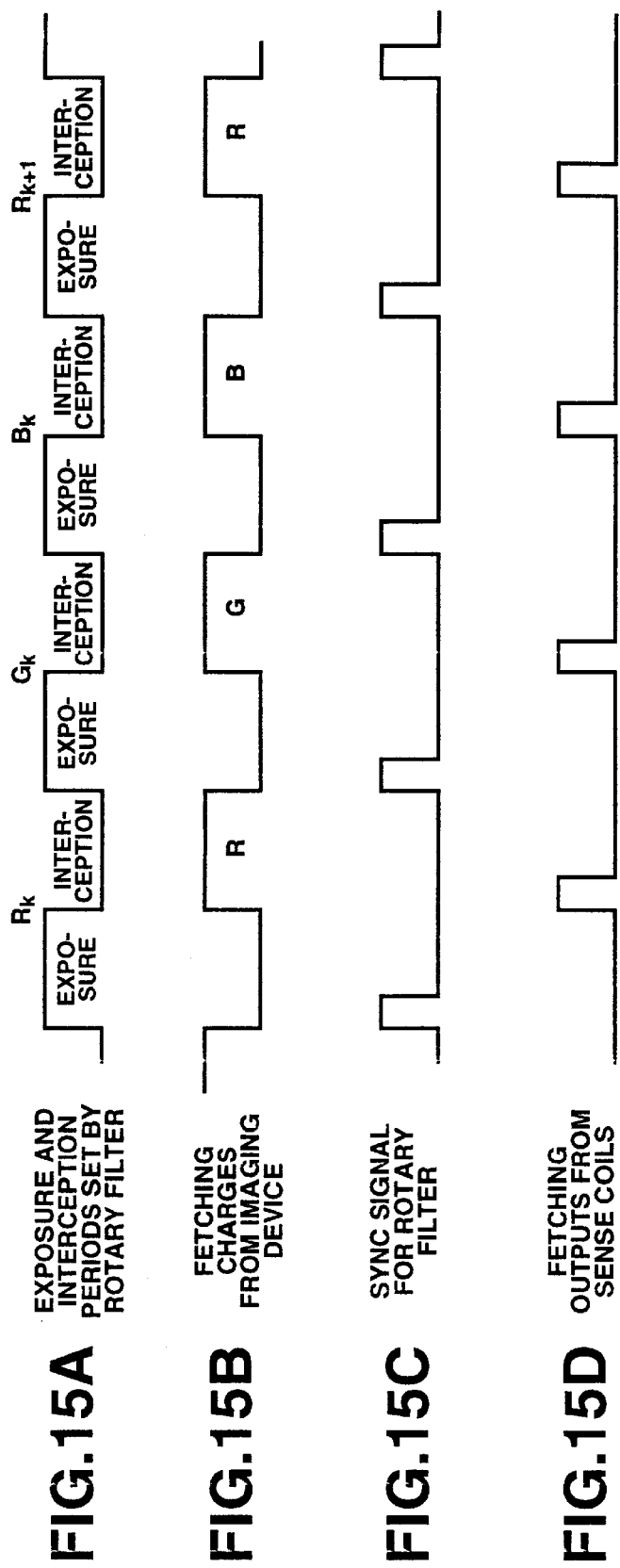

ENDOSCOPIC IMAGE PROCESSING SYSTEM CAPABLE OF ESTIMATING ABSOLUTE SHAPE OF OBJECT ENTITY

BACKGROUND OF THE INVENTION

1. Field of the Invention

The present invention relates to an endoscopic image processing system. More particularly, this invention is concerned with an endoscopic image processing system including a shape estimating unit for estimating the absolute shape of an object entity according to images of the same object entity produced at different positions.

2. Description of the Related Art

Assume that a plurality of imaging means are arranged so that the fields of view offered by the imaging means will overlap and that the relative locations of the imaging means are known. Under the circumstances, the question of how to estimate the shape of an object according to produced images is treated as the question of estimating a shape from so-called stereoscopic images. Various methods have been proposed for overcoming the question.

In recent years, some proposals have been made for a method of extracting a three-dimensional structure from motions. This method is construed as a technique attempting to estimate relative movements of an imaging means using a plurality of images.

The methods employ as raw information association of the positions of the same point on an object appearing in a plurality of images.

Various methods have been proposed of the way of detecting the positions of the same point on an object appearing in images. In the case of artificial objects, components of angles and a contour are often apparent. A technique of extracting a structure including line segment extraction would prove effective. However, there is difficulty in adapting the technique to ordinary natural images. Density gradient is a technique often adapted to time-sequential images. This technique provides good results when an apparent movement of an object observed between images is very small and image quality is good. However, many restrictions are imposed on the conditions for imaging.

In general, therefore, an area surrounding a point concerned in an image is extracted as a reference area. The reference area is correlated with an area extracted from an image of an object of search. A position giving a maximum correlation value is regarded as a corresponding point. This technique (block matching) is often adopted. Block matching provides relatively stable results as long as the texture of an image is clear. If the texture is unclear, an incorrect corresponding point may be detected.

Furthermore, a primary drawback of the block matching technique lies in that when an object is three-dimensional and a boundary relative to a background is contained in a block, the results of detection are unreliable. Moreover, the surface of an object may be inclined relative to an imaging means or the distances from a plurality of imaging means to the object may be mutually different. Images produced by the plurality of imaging means may visualize the object as a substantially deformed object. Also, there may be large differences in size among the images. In any of these cases, the results of detection are unreliable.

A question concerning estimation of a three-dimensional shape is the question of occlusion or of matching the results of estimation. In particular, when stereoscopic images are used for estimation, a portion of an object may be hidden and therefore not be imaged or a portion thereof may be imaged by only one imaging means. This the question of how to treat these arises.

If the number of imaging means is large, the number of areas to be imaged becomes accordingly large. The number of hidden areas is limited. However, when the positions of imaging means are unknown or estimation is not carried out accurately, it is not easy to match images.

Not almost all conventionally proposed techniques can be said to be fully satisfactory in terms of practice abilities. This is because the techniques are concerned with images of an artificial object. These techniques attempt to address the foregoing questions, which arise without fail when a natural object is imaged, on the presumption or condition that influence is ignored or underestimated.

For example, images produced by a biomedical endoscope are images for which it is hard to adapt the conventionally proposed techniques. However, if the techniques properly functioned on the images, they would prove very valuable in practice.

Endoscopes have an elongated insertion unit which is inserted into a body cavity, whereby a lesion or the like in the body cavity can be observed without incision or can be cured or treated using, if necessary, a treatment appliance. The size of the distal part of an endoscope must be minimized from a functional viewpoint. Any members other than those required by a doctor for observation or treatment cannot therefore be incorporated in the distal part.

Some proposals have already been made of grasping the shape of an object trans-endoscopically. Proposed are, for example, a method of projecting patterned light or the like on an object of observation (Japanese Unexamined Patent Publication No. 63-240831), and a system having a compound eye incorporated in the distal part of an endoscope (Japanese Unexamined Patent Publication No. 63-244011). In either case, a special structure must be formed in the distal part of an endoscope or in a light source unit. This leads to a large or complex endoscopic system. In general, the method and system can therefore not be easily adopted.

Japanese Unexamined Patent Publication No. 63-246716 filed by the same applicant has disclosed a technique of estimating the shape of an object using a plurality of images produced by moving the distal part of an endoscope through manipulations. Also disclosed is a measuring mechanism for measuring magnitude of shifts made by the distal part responsively to manipulations. According to this technique, the absolute shape of an object can be estimated without impairment of the functions of an existing endoscope.

Moreover, Japanese Unexamined Patent Publication No. 6-7289 filed by the same applicant has disclosed a technique of estimating the relative shapes of an object and reference entity using a plurality of images produced by moving the distal part of an endoscope through manipulations. Also disclosed is a technique of estimating the size of an object according to the size of a reference entity located near the object.

According to the constituent features of the foregoing Japanese Unexamined Patent Publication No. 63-246716, the relative shapes of an object entity are estimated using a plurality of images produced time-sequentially. Magnitudes of shift made by an imaging means incorporated in the distal part of an endoscope responsively to the manipulations are measured. The absolute shape of the object is then estimated based on the measured value.

However, precision offered by the measuring mechanism is neither insufficient nor sufficient in terms of the resolution an imaging means is desired to provide.

Moreover, according to the constituent features of the Japanese Unexamined Patent Publication No. 6-7289, when an object entity is imaged time-sequentially, a reference entity having a size is known is imaged concurrently with the object entity. The absolute shape of the object entity is thus drawn out.

However, when a biomedical endoscope is used to concurrently image the object entity and the reference entity placed near the object entity, an operator of the endoscope has a large burden.

Japanese Unexamined Patent Publication No. 9-26547 has proposed an endoscopic system capable of precisely estimating an absolute distance from an imaging means to an object entity using images of the same object entity produced at different positions.

However, in the Japanese Unexamined Patent Publication No. 9-26547, the relative shapes are estimated using images of the object entity produced at different positions. Images exhibiting halation or images produced when laser light has been irradiated are used to calculate a distance between the distal part of an endoscope and an object and to thus estimate the absolute shape of the object. This poses a problem in that precision varies depending on the states of images employed in the calculation of a distance.

SUMMARY OF THE INVENTION

An object of the present invention is to provide an endoscopic image processing system capable of precisely estimating the absolute shape of an object entity irrespective of the states of images.

Another object of the present invention is to provide an endoscopic image processing system capable of accurately grasping the absolute shape of an object entity by accurately synchronizing image data with position data.

An endoscopic image processing system in accordance with the present invention comprises an image, an image memory, a relative shape estimating means, a first coil means, a position information detection, a position information acquiring unit, and a subject shape estimation. The images produces endoscopic images of a subject through an objective. The image memory stores a plurality of images produced by the images. The relative shape estimation estimates the relative shapes of the subject appearing in a plurality of images using image signals representing the images stored in the image memory. The first coil is located near the objective. The position information detection has a second coil fixed at a predetermined position therein and detects positions of the first coil by utilizing magnetic fields. The position information acquiring unit acquires position information of the positions detected by the position information detection in association with the respective images stored in the image information memory means. The subject shape estimator estimates the shape of the subject according to the shape information of the relative shapes estimated by the relative shape estimation and the position information acquired by the position information acquiring unit.

In the endoscopic image processing system of the present invention, the position information acquiring unit acquires position information of the positions detected by the position information detection in association with the respective images stored in the image information memory. The subject shape estimator estimates the shape of the subject according to the shape information of the relative shapes estimated by the relative shape estimator and the position information acquired by the position information acquiring unit. The absolute shape of the object entity can thus be estimated precisely irrespective of the states of images.

Other features and advantages of the present invention will be fully apparent from the description below.

BRIEF DESCRIPTION OF THE DRAWINGS

FIG. 1 to FIG. 13 relate to a first embodiment of the present invention;

FIG. 1 shows the configuration of an endoscopic system;

FIG. 2 is a block diagram showing the functional configuration of an endoscopic position detecting apparatus shown in FIG. 1;

FIG. 3 shows the configuration of the endoscopic position detecting apparatus shown in FIG. 2;

FIG. 4 shows the configuration of a two-port memory and others constituting a major portion of the endoscopic position detecting apparatus shown in FIG. 3;

FIG. 5 is a timing chart indicating the operations of the two-port memory shown in FIG. 4;

FIG. 6 shows the configuration of an image processing apparatus shown in FIG. 1;

FIG. 7 is a first explanatory diagram for explaining the principles of calculating the coordinates of the estimated position of a source coil included in the endoscopic position detecting apparatus shown in FIG. 3;

FIG. 8 is a second explanatory diagram for explaining the principles of calculating the coordinates of the estimated position of the source coil included in the endoscopic position detecting apparatus shown in FIG. 3;

FIG. 9 is a third explanatory diagram for explaining the principles of calculating the coordinates of the estimated position of the source coil included in the endoscopic position detecting apparatus shown in FIG. 3;

FIG. 10 is a first explanatory diagram for explaining operations performed by the image processing apparatus shown in FIG. 6;

FIG. 11 is a second explanatory diagram for explaining the operations performed by the image processing apparatus shown in FIG. 6;

FIG. 13 is a flowchart describing the flow of processing steps performed by the image processing apparatus shown in FIG. 6;

FIG. 14 to FIG. 15D relate to the second embodiment of the present invention;

FIG. 14 shows the structure of a rotary filter; and

FIG. 15A is a first timing chart indicating the timing of each signal relative to a sync signal synchronous with the rotary filter shown in FIG. 14;

FIG. 15B is a second timing chart indicating the timing of each signal relative to a sync signal synchronous with the rotary filter shown in FIG. 14;

FIG. 15C is a third timing chart indicating the timing of each signal relative to a sync signal synchronous with the rotary filter shown in FIG. 14; and FIG. 15D is a fourth timing chart indicating the timing of each signal relative to a sync signal synchronous with the rotary filter shown in FIG. 14.

DESCRIPTION OF THE PREFERRED EMBODIMENTS

Embodiments of the present invention will be described with reference to the drawings.

Figure 1:
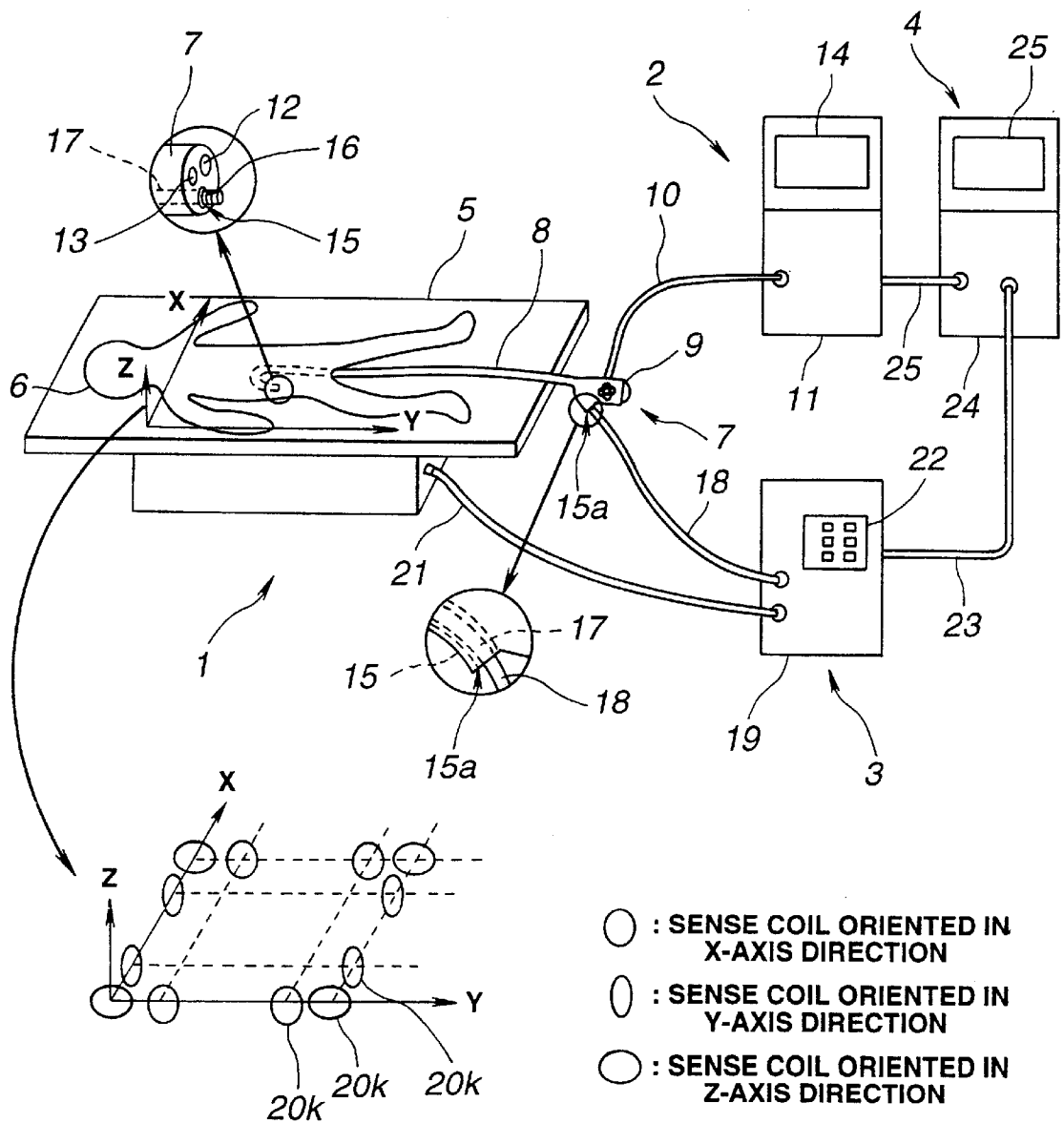

As shown in FIG. 1, an endoscopic system 1 of this embodiment comprises an endoscope system 2, an endoscopic position detecting apparatus 3, and an image processing apparatus 4. The endoscope system 2 enables endoscopic examinations. The endoscopic position detecting apparatus 3 detects the three-dimensional positions of the distal part of an endoscope in a body cavity. The image processing apparatus 4 estimates the shape of an object entity visualized by the endoscope.

Herein, the image processing apparatus 4 is used to obtain the shape of an object entity in a body cavity. For this purpose, an insertion unit 8 of an electronic endoscope 7 is inserted into the body cavity of a patient 6 lying down on a patient couch 5.

The electronic endoscope 7 has an operation unit 9 formed at the back end of the elongated insertion unit 8 having plasticity. The operation unit 9 has an angling knob. A universal cord 10 is extended from the operation unit 9 and coupled to a video imaging system (video processor) 11. The endoscope system 2 preferably consists of the electronic endoscope 7 and video processor 11.

A light guide extends through the electronic endoscope 7. Illumination light emanating from a light source unit in the video processor 11 is transmitted via the light guide. The transmitted illumination light is emitted through an illumination window 12 formed in the distal end of the insertion unit 8, thus illuminating a patient or the like. Light reflected from an illuminated lesion or any other subject passes through an objective fitted in an observation window 13 adjoining the illumination window, and forms an image on an imaging device. The imaging device lies on the image plane of the objective and has a color filter. The imaging device photoelectrically converts the light image.

A signal resulting from the photoelectric conversion is processed by a video signal processing unit in the video processor 11. A standard video signal ensues. An image is displayed on an image observation monitor 14 connected to the video processor 11.

The electronic endoscope 7 has a forceps channel 15 formed therein. A probe 17 having, for example, one magnetic generation element (or source coil) 16 is passed through an insertion port 15a of the forceps channel 15. The source coil 16 is thus placed in the distal part of the electronic endoscope 7.

A source cable 18 extending from the back end of the probe 17 has a connector spliced to the back end thereof. The connector is coupled to a main unit 19 of the endoscopic position detecting apparatus 3 so that it can be uncoupled freely. A high-frequency signal (driving signal) is applied from the main unit 19 to the source coil 16 serving as an magnetic generator means over the source cable 18 serving as a high-frequency signal transmitter. Electromagnetic waves including vibrating magnetic fields are thus radiated around the source coil 16.

Moreover, a plurality of magnetic detecting elements (or sense coils) 20k are incorporated at predetermined positions in the patient couch 5 on which the patient 6 lies down. Preferably, a total of 12 single-core coils 20k is are divided into four sets of three single-core coils. The three single-core coils are oriented in the same directions as the X, Y, and Z axes of a coordinate system defined with the patient couch 5 as a reference.

The sense coils 20k are connected to the main unit 19 of the endoscopic position detecting apparatus 3 over a sense cable 21 serving as a detected signal transmitter via a connector formed on the patient couch 5. The main unit 19 includes an operator panel 22 or keyboard which a user manipulates to operate the apparatus. Moreover, the main unit 19 is connected to a main unit 24 of the image processing apparatus 4 over a cable 23. Thus, data is transmitted or received to or from the apparatuses.

Moreover, the main unit 24 of the image processing apparatus 4 is connected to the video processor 11 over a cable 25. The main unit 24 thus receives an image signal (red, green, and blue signals and a sync signal) from the video processor 11. The main unit 24 of the image processing apparatus 4 estimates the relative shapes of an object entity using successive image signals sent from the video processor 11. The main unit 24 then calculates the absolute shape of the object entity using position data of the distal part of the electronic endoscope 7 sent from the main unit 19 of the endoscopic position detecting apparatus 3.

Furthermore, the main unit 24 of the image processing apparatus 4 produces two-dimensional data of the object entity observed from any observing point and displays an image on the monitor 25 according to the data.

Figure 2:
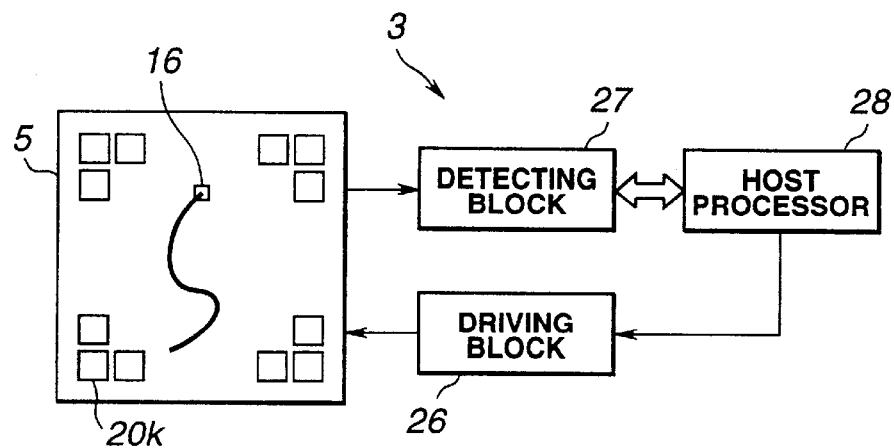

The endoscopic position detecting apparatus 3 consists, as shown in FIG. 2, of a driving block 26, a detecting block 27, and a host processor 28. The driving block 26 activates the source coil 16. The detecting block 27 detects signals received by the sense coils 20k. The host processor 28 processes a signal detected by the detecting block 27.

Figure 3:
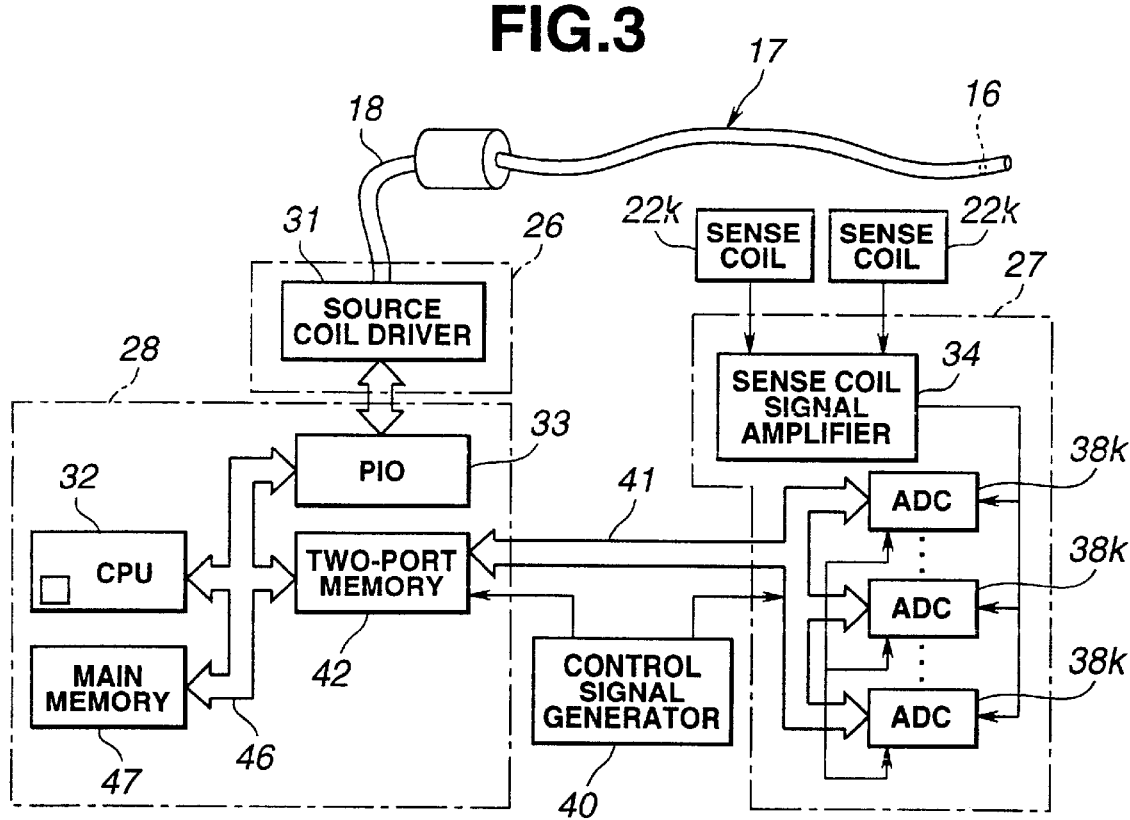

As shown in FIG. 3, the probe 17 extending through the insertion unit 8 of the electronic endoscope 7 includes the source coil 16 for generating magnetic fields. The source coil 16 is connected to a source coil driver 31 for producing a high-frequency driving signal. The source coil driver 31 part of the driving block 26.

The source coil driver 31 drives the source coil 16 with a sine-wave current driving signal. The frequency of the driving signal is determined with driving frequency setting data (or driving frequency data). The driving frequency setting data is saved in a driving frequency setting data storage unit or driving frequency setting data memory, which is not shown, incorporated in the source coil driver 31. The data of the driving frequency is stored in the driving frequency data storage unit (not shown) incorporated in the source coil driver 31. Beforehand, the driving frequency data is passed through a parallel input/output circuit (PIO) 33 by a central processing unit (CPU) 32 incorporated in the host processor 28. The CPU 32 detects the three-dimensional positions of the distal part of the electronic endoscope 6.

The, twelve sense coils 20k are connected to a sense coil signal amplifier 34 included in the detecting block 27.

Figure 4:
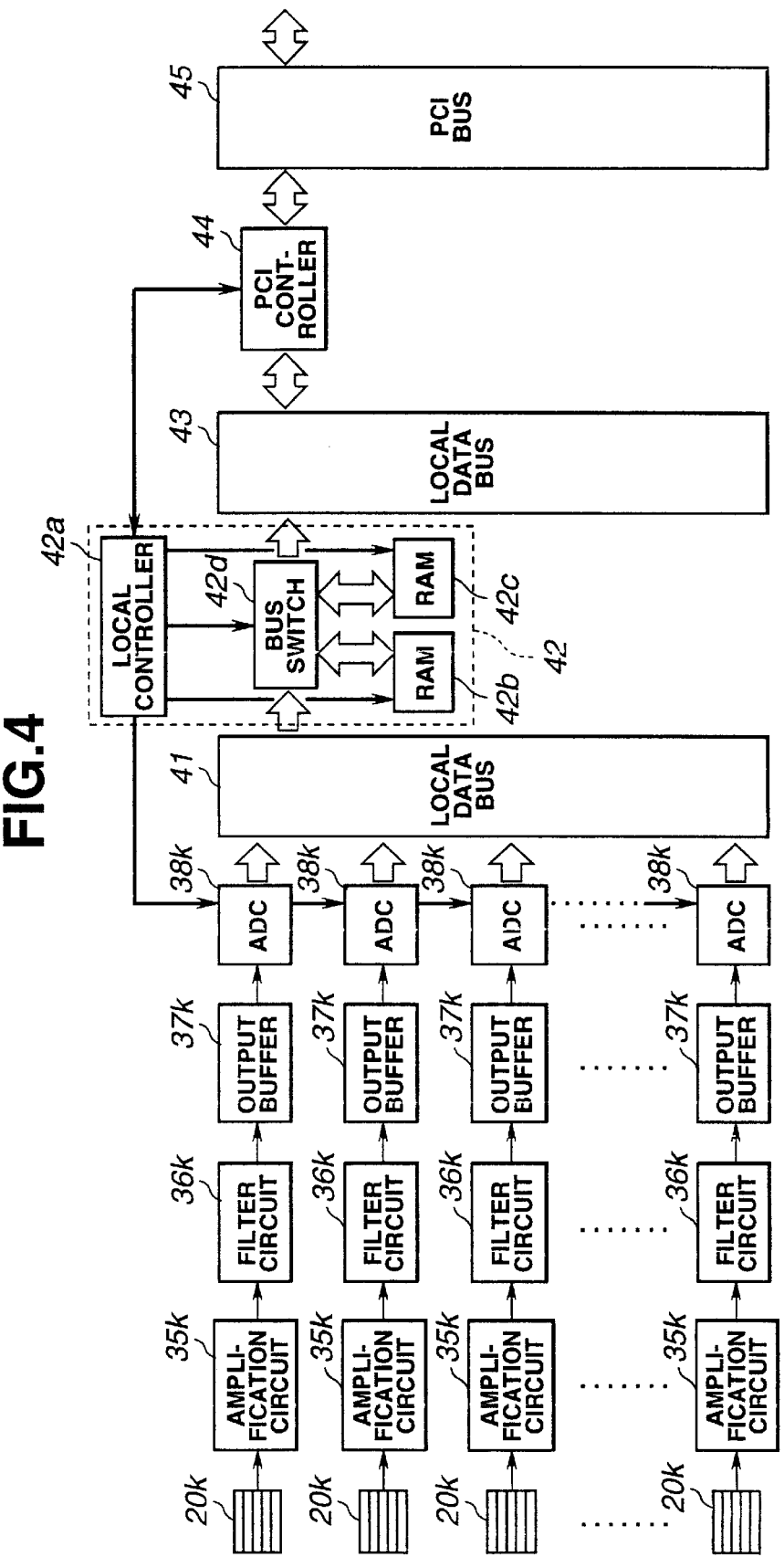

As shown in FIG. 4, in the sense coil signal amplifier 34, the sense coils 20k are connected to amplification circuits 35k in one-to-one correspondence therewith 20k. Microscopic signals detected by the sense coils 20k are amplified by the amplification circuits 35k and filtered by filter circuits 36$k$. The, signals having unnecessary components, which fall within a frequency band of waves generated by the source coil 16 are, removed by the filter circuits 36$k$, and then output to output buffers 7$k$. Thereafter, the signals are converted into digital signals readable by the host processor 28 by way of analog-to-digital converters (ADC) 38$k$.

The detecting block 27 consists of the sense coil signal amplifier 34 and ARCS 38$k$. The sense coil signal amplifier 34 consists of the amplification circuits 35$k$, filter circuits 36$k$, and output buffers 37$k$.

Referring back to FIG. 3, outputs of the twelve channels of the sense coil signal amplifier 34 are transmitted to the twelve ARCS 38$k$. The outputs are then converted into digital data at a predetermined sampling rate specified with a clock supplied from a control signal generator 40. The digital data is written in the two-port memory 42 over a local data bus 41 in response to a control signal sent from the control signal generator 40.

Figure 5:
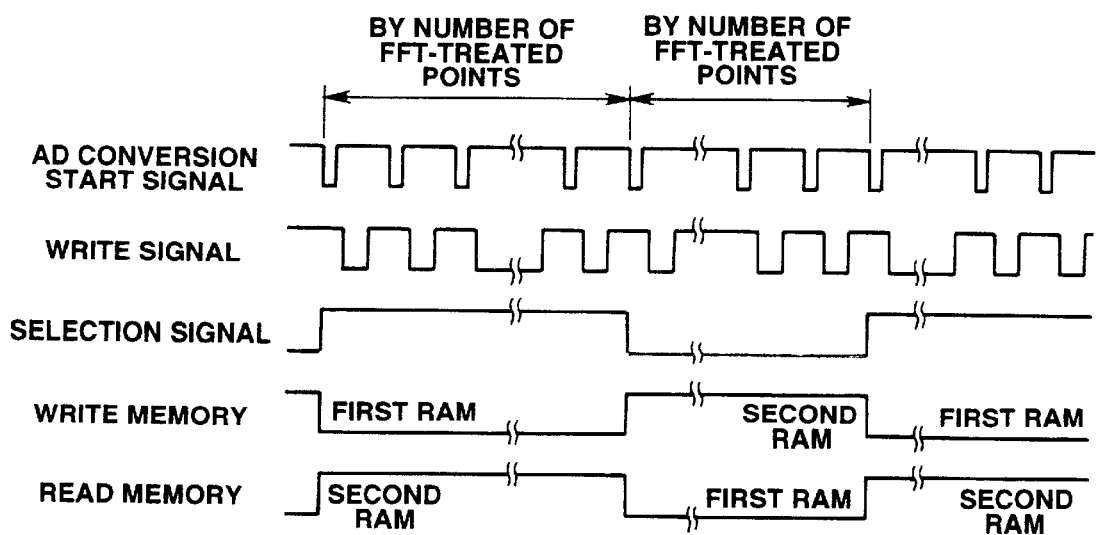

The two-port memory 42 consists, as shown in FIG. 4, of a local controller 42$a$, a first RAM 42$b$, a second RAM 42$c$, and a bus switch 42$d$. According to the timing indicated in FIG. 5, the ADCs 38$k$ start analog-to-digital conversion in response to an analog-to-digital conversion start signal sent from the local controller 42$a$. The bus switch 42$d$ switches the first RAM 42$b$ and second RAM 42$c$ according to a selection signal sent from the local controller 42$a$. The first RAM 42$b$ and second RAM 42$c$ alternately serve as a read memory and write memory. After the power supply is turned on, data is always fetched in response to a write signal.

Referring to FIG. 3, the CPU 32 reads digital data written in the two-port memory 42 in response to a control signal sent from the control signal generator 27 over an internal bus 46. The internal bus 46 is composed of a local data bus 43, a PCI controller 44, and a PCI bus 45 (See FIG. 4). The CPU 32 performs frequency extraction (Fast Fourier Transform (FFT)) on the digital data using a main memory 47. The CPU 32 then separates and extracts magnetic field detection information having one or more components frequency corresponding to the driving frequency of the source coil 16. The CPU 32 then calculates the coordinates of the spatial position of the distal part of the electronic endoscope 7 using the digital data of the separated magnetic field detection information.

The CPU 32 calculates the magnetic field detection information having frequency components corresponding to the driving frequency of the source coil 16, that is, electromotive forces (amplitudes of sine-wave signals) developed at the sense coils 20$k$, and phase information. The phase information indicates the positive or negative polarity of each electromotive force.

Figure 6:
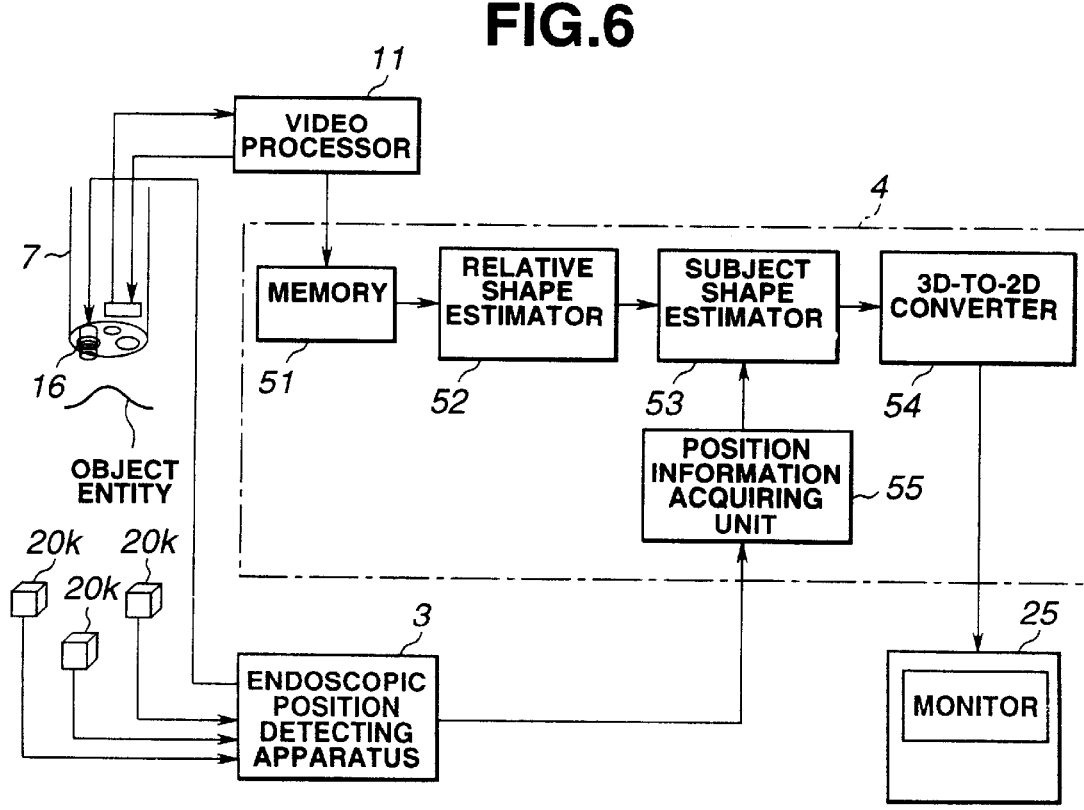

The image processing apparatus 4 will be described below. As shown in FIG. 6, the image processing apparatus 4 converts an image signal sent from the video processor 11 into digital data, and stores the digital data as image data successively in a memory 51. The image data stored in the memory 51 is sent to a relative shape extamator 52. The relative shape estimator 52 estimates the relative shapes of an object entity.

Data representing the position in a three-dimensional space of the source coil 16 detected by the endoscopic position detecting apparatus 3 is sent to a position information acquiring unit 55. The position information acquiring unit 55 calculates magnitudes of shifts observed in images used to estimate the relative shapes of the object entity.

Moreover, a subject shape estimator 53 estimates the absolute shape of the object entity according to the magnitude of shifts calculated by the position information acquiring unit 55 and the relative shapes estimated by the relative shape estimator 52.

Image data representing an image that depicts the shape estimated by the subject shape estimator 53 and observed from any observing point is produced by a 3D-to-2D converter 54. The image represented by the image data is then displayed on a monitor 25.

As shown in FIG. 1, the source coil 16 passing through the insertion port 15$a$ of the forceps channel extending through the electronic endoscope 7 is locked in the distal part of the insertion unit 8. The distal part is moved relative to the same object entity by manipulating the operation unit 9 of the electronic endoscope 7.

As soon as the distal part of the electronic endoscope 7 moves relative to the object entity, the endoscopic position detecting apparatus 3 detects the position of the distal part of the electronic endoscope 7 (position of the source coil 16). In addition, an input unit such as the operator panel 22 included in the image processing steps apparatus 4 is used to execute the processing of estimating the absolute shape of the object entity.

Figure 7:
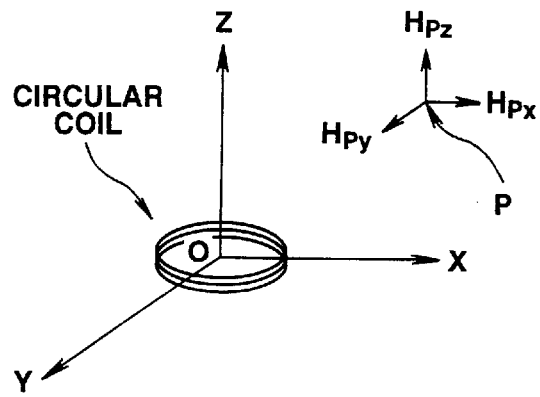

Operations performed by the endoscopic position detecting apparatus 3 will now be described. Additional details may be found in the Japanese Unexamined Patent Publication No. 10-69075 filed by the present applicant. As shown in FIG. 7, assume that a circular coil has a very small radius. When a current flows into the circular coil, a magnetic potential develops at a point P in a three-dimensional space similar to that of a magnetic dipole. The magnetic potential is expressed by the following formula:

$$U_P = \frac{\mu I N_1 \pi a^2}{4\pi\mu} \frac{z}{(x^2+y^2+z^2)^{\frac{3}{2}}} \tag{1}$$

where $\mu$ denotes a magnetic permeability, $N_1$ denotes the number of turns of the circular coil, a denotes the radius of the circular coil, and I denotes a current flowing into the circular coil.

Accordingly, magnetic fields ($H_{px}$, $H_{py}$, $H_{pz}$) oriented in the same directions as the X, Y, and Z axes are induced at point P. The magnetic fields are calculated as follows:

$$H_{Px} = -\frac{\partial U_P}{\partial x} = \frac{IN_1 a^2}{4} 3 \frac{xz}{(x^2+y^2+z^2)^{\frac{5}{2}}} = k_g 3 \frac{xz}{r^5} \tag{2}$$

$$H_{Py} = -\frac{\partial U_P}{\partial y} = \frac{IN_1 a^2}{4} 3 \frac{yz}{(x^2+y^2+z^2)^{\frac{5}{2}}} = k_g 3 \frac{yz}{r^5}$$

$$H_{Pz} =$$

$$-\frac{\partial U_P}{\partial z} = \frac{IN_1 a^2}{4} 2z^2 - x^2 - \frac{y^2}{(x^2+y^2+z^2)^{\frac{5}{2}}} = k_g 2z^2 - x^2 - \frac{y^2}{r^5}$$

Figure 8:
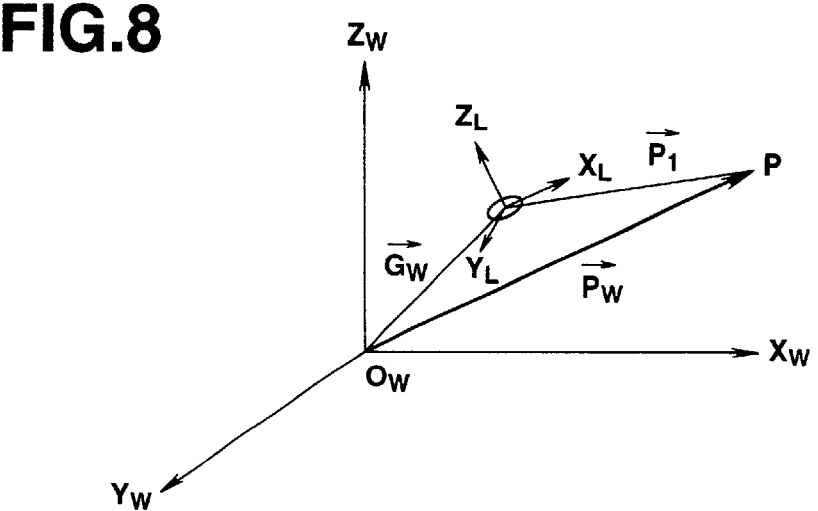

In the three-dimensional space like the one shown in FIG. 8 (hereinafter, a world coordinate system $X_w$—$Y_w$—$Z_w$), the position of a single-core coil (hereinafter a source coil) for generating magnetic fields shall be expressed by ($X_{gw}$, $Y_{gw}$, $Z_{gw}$) Any position in the three-dimensional space may be regarded as point P ($X_{pw}$, $Y_{pw}$, $Z_{pw}$)

Assuming that a coordinate system defined with the source coil as a reference is regarded as a local coordinate system $X_L$—$Y_L$—$Z_L$, the coordinates ($X_{p1}$, $Y_{p1}$, $Z_{p1}$) of point P in the local coordinate system are defined as follows:

$$P_l = R^{-1}(P_W - G_W) \qquad (3)$$

$$\begin{pmatrix} x_{Pl} \\ y_{Pl} \\ z_{Pl} \end{pmatrix} = \begin{pmatrix} R_{00} & R_{10} & R_{20} \\ R_{01} & R_{11} & R_{21} \\ R_{02} & R_{12} & R_{22} \end{pmatrix} \begin{pmatrix} x_{PW} - x_{gW} \\ y_{PW} - y_{gW} \\ z_{PW} - z_{gW} \end{pmatrix}$$

where $P_1$ denotes a vector directed from an origin O to the point P in the local coordinate system, $P_w$ denotes a vector directed from the origin O to the point P in the world coordinate system, $G_w$ denotes a vector directed to the position of the source coil in the world coordinate system, and R denotes a rotational matrix.

Figure 9:
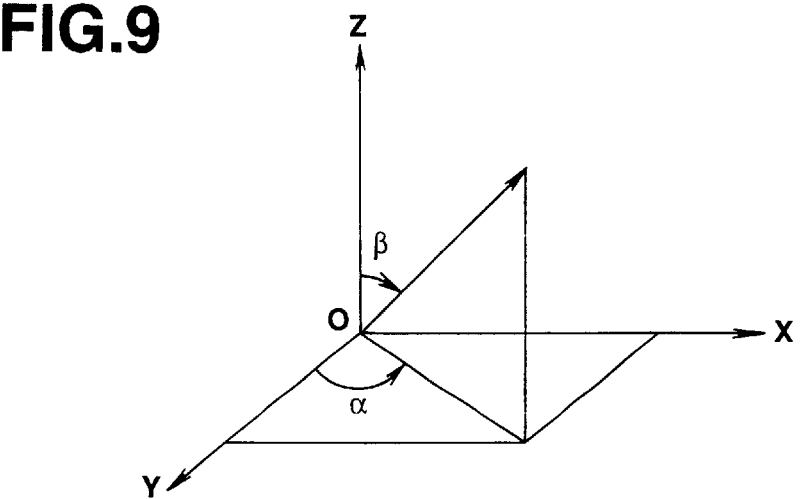

Herein, the rotational matrix R in the polar coordinate system shown in FIG. 9 is defined as follows:

$$R = \begin{pmatrix} R_{00} & R_{01} & R_{02} \\ R_{10} & R_{11} & R_{12} \\ R_{20} & R_{21} & R_{22} \end{pmatrix} = \begin{pmatrix} \cos\alpha & \sin\alpha\cos\beta & \sin\alpha\sin\beta \\ -\sin\alpha & \cos\alpha\cos\beta & \cos\alpha\sin\beta \\ 0 & -\sin\beta & \cos\beta \end{pmatrix} \qquad (4)$$

where $\alpha$ denotes a magnitude of rotation made with the $Z_w$ axis as a center, and $\beta$ denotes a magnitude of rotation made with the $X_w$ axis as a center.

In the local coordinate system defined with the source coil as a reference, the magnetic fields H1 ($H_{px1}$, $H_{py1}$, $H_{pz1}$) developed at point P are defined based on the formula (3) as follows:

$$H_{Pxl} = \frac{k_g}{r^5} 3x_{Pl}z_{Pl} \qquad (5)$$

$$H_{Pyl} = \frac{k_g}{r^5} 3y_{Pl}z_{Pl}$$

$$H_{Pzl} = \frac{k_g}{r^5} (2z_{Pl}^2 - x_{Pl}^2 - y_{Pl}^2)$$

The magnetic fields $H_w$ ($H_{pxw}$, $H_{pyw}$, $H_{pzw}$) oriented in the same directions as the $X_w$, $Y_w$, and $Z_w$ axes at point P in the world coordinate system are expressed as follows:

$$H_W = RH_l \qquad (6)$$

$$H_{PxW} = \frac{k_g}{r^5}[\{2(x_{PW} - x_{gW})^2 - (y_{PW} - y_{gW})^2 - (z_{PW} - z_{gW})^2\}\sin\alpha\sin\beta +$$
$$3(y_{PW} - y_{gW})(x_{PW} - x_{gW})\cos\alpha\sin\beta +$$
$$3(z_{PW} - z_{gW})(x_{PW} - x_{gW})\cos\beta]$$

$$H_{PyW} = \frac{k_g}{r^5}[3(x_{PW} - x_{gW})(y_{PW} - y_{gW})\sin\alpha\sin\beta +$$
$$\{2(y_{PW} - y_{gW})^2 - (z_{PW} - z_{gW})^2 - (x_{PW} - x_{gW})^2\}\cos\alpha\sin\beta +$$
$$3(z_{PW} - z_{gW})(y_{PW} - y_{gW})\cos\beta]$$

$$H_{PzW} = \frac{k_g}{r^5}[3(x_{PW} - x_{gW})(z_{PW} - z_{gW})\sin\alpha\sin\beta +$$
$$3(y_{PW} - y_{gW})(z_{PW} - z_{gW})\cos\alpha\sin\beta] +$$
$$\{2(z_{PW} - z_{gW})^2 - (y_{PW} - y_{gW})^2 - (x_{PW} - x_{gW})^2\}\cos\beta]$$

Assuming that one source soil for generating magnetic fields in the three-dimensional space XYZ is located at a position ($x_g$, $y_g$, $z_g$) in a direction ($g_x$, $g_y$, $g_z$), the magnetic fields $H_x$, $H_y$, $H_z$ developed at an appropriate position P ($x_d$, $y_d$, $z_d$) are expressed based on the formula (6) as follows:

$$\begin{pmatrix} H_x \\ H_y \\ H_z \end{pmatrix} = \frac{k_s}{r^5} \begin{pmatrix} 2(x_d - x_g)^2 - (y_d - y_g)^2 - (z_d - z_g)^2 & 3(y_d - y_g)(x_d - x_g) & 3(z_d - z_g)(x_d - x_g) \\ 3(x_d - x_g)(y_d - y_g) & 2(y_d - y_g)^2 - (z_d - z_g)^2 - (x_d - x_g)^2 & 3(z_d - z_g)(y_d - y_g) \\ 3(x_d - x_g)(z_d - z_g) & 3(y_d - y_g)(z_d - z_g) & 2(z_d - z_g)^2 - (y_d - y_g)^2 - (x_d - x_g)^2 \end{pmatrix} \begin{pmatrix} g_x \\ g_y \\ g_z \end{pmatrix} \qquad (7)$$

where $k_s$ denotes a constant, and r denotes a distance from the source coil to point P. Moreover, the orientations of the magnetic fields $H_x$, $H_y$, and $H_z$ are the same as those of the X, Y, and Z axes.

Assuming that single-core coils $C_x$, $C_y$, and $C_z$ oriented in the same directions as the coordinate axes X, Y, and Z are placed at point P, voltages $V_x$, $V_y$, and $V_z$ developed at the single-core coils $C_x$, $C_y$, and $C_z$ are expressed as follows:

$$\begin{pmatrix} V_x \\ V_y \\ V_z \end{pmatrix} = \frac{k_1}{r^5} \begin{pmatrix} 2(x_d - x_g)^2 - (y_d - y_g)^2 - (z_d - z_g)^2 & 3(y_d - y_g)(x_d - x_g) & 3(z_d - z_g)(x_d - x_g) \\ 3(x_d - x_g)(y_d - y_g) & 2(y_d - y_g)^2 - (z_d - z_g)^2 - (x_d - x_g)^2 & 3(z_d - z_g)(y_d - y_g) \\ 3(x_d - x_g)(z_d - z_g) & 3(y_d - y_g)(z_d - z_g) & (z_d - z_g)^2 - (y_d - y_g)^2 - (x_d - x_g)^2 \end{pmatrix} \begin{pmatrix} g_x \\ g_y \\ g_z \end{pmatrix} \quad (8)$$

Herein, the single-core coil $C_x$ oriented along the X axis is a coil whose shaft is oriented in the same direction as the X axis. A lead wire is wound about the shaft in order to form the coil. The single-core coils $C_y$ and $C_z$ oriented in the same directions as the Y and Z axes are also similar coils.

As shown in FIG. 1, in this embodiment, a plurality of sense coils 20k having single-core coils are arranged in a three-dimensional space. More particularly, four sense coils oriented along the X axis, four sense coils oriented along the Y axis, and four sense coils oriented along the Z axis (amounting to twelve sense coils 20k) are arranged in the patient couch 5. The voltages developed at the twelve sense coils 20k, and the positions and orientations of the twelve sense coils 20k are thus known. Twelve nonlinear equations having the position $(x_g, y_g, z_g)$ and orientation $(g_x, g_y, g_z)$ of the source coil 16 as unknown quantities can therefore be defined based on the formula (8).

The solutions of the twelve nonlinear equations, that is, the position and orientation of the source coil 16 are calculated according to a method of iteration and modification (Gauss-Newton method).

Assume that x is a parameter specifying the position $(x_g, y_g, z_g)$ and orientation $(g_x, g_y, g_z)$ of the source coil, and that the initial value of the parameter is $x^{(0)}$.

Assume that a k-order estimated value $x^{(k)}$ is worked out according to the iteration and modification, and that a model function $V(x)$ expressing power developed at the sense coils is developed as a Taylor's series within $x^{(k)}$. A resultant linear approximate value is expressed as follows:

$$V(x) = V(x^{(k)}) + \left[\frac{\partial V(x)}{\partial x}\right]_{x=x^{(k)}} (x - x^{(k)}) \quad (9)$$

Assuming that Vm denotes a voltage measured by each sense coil, an observation equation is defined as the formula below.

$$Vm(x) \cong V(x^{(k)}) + \left[\frac{\partial V(x)}{\partial x}\right]_{x=x^{(k)}} (x - x^{(k)}) \quad (10)$$

Note that the left and right sides of the formula are not equal to each other but nearly equal thereto because Vm contains a measurement error.

When the first term of the right side of the formula (10) is moved to the left side, $$\Delta Vm^{(k)} \cong A^{(k)} \Delta x^{(k)} \quad (11)$$

Herein, $$\Delta Vm^{(k)} = vm - v(x^{(k)}) = Vm - Vm^{(k)} \quad (12)$$

$$\Delta x^{(k)} = x - x^{(k)} \quad (13)$$

$$A_{ij} = \left[\frac{\partial V_i(x)}{\partial x_j}\right]_{x=x^{(k)}} \quad (14)$$

where i ranges from 1 to n, and j ranges from 1 to m. Note that the number of unknown quantities in the rows is n and the number of sense coils in the columns is m. The solution $\Delta x^{(k)}$ is defined based on the formula (11) as follows:

$$\Delta x^{(k)} = (B^{(k)} W A^{(k)})^{-1} B^{(k)} W \Delta Vm^{(k)} \quad (15)$$

where B denotes a transposed matrix of A, and W denotes a weight matrix.

An estimated value of a modified parameter is calculated based on the formula (13) as follows:

$$x^{(k+1)} = x^{(k)} + \Delta x^{(k)} \quad (16)$$

When the twelve sense coils 20k are arranged as shown in FIG. 1, the matrix A is defined as the formula (17) below.

$$A = \begin{bmatrix} \frac{\partial V_{x0}}{\partial x_g} & \frac{\partial V_{x0}}{\partial y_g} & \frac{\partial V_{x0}}{\partial z_g} & \frac{\partial V_{x0}}{\partial g_x} & \frac{\partial V_{x0}}{\partial g_y} & \frac{\partial V_{x0}}{\partial g_z} \\ \frac{\partial V_{x1}}{\partial x_g} & \frac{\partial V_{x1}}{\partial y_g} & \frac{\partial V_{x1}}{\partial z_g} & \frac{\partial V_{x1}}{\partial g_x} & \frac{\partial V_{x1}}{\partial g_y} & \frac{\partial V_{x1}}{\partial g_z} \\ \vdots & \vdots & \vdots & \vdots & \vdots & \vdots \\ \frac{\partial V_{z11}}{\partial x_g} & \frac{\partial V_{z11}}{\partial y_g} & \frac{\partial V_{z11}}{\partial z_g} & \frac{\partial V_{z11}}{\partial g_x} & \frac{\partial V_{z11}}{\partial g_y} & \frac{\partial V_{z11}}{\partial g_z} \end{bmatrix} \quad (17)$$

The weight matrix W is defined as follows:

$$W = \begin{bmatrix} \sigma_0^2 & 0 & 0 & \cdots & 0 \\ 0 & \sigma_1^2 & 0 & \cdots & 0 \\ 0 & 0 & \sigma_2^2 & \cdots & 0 \\ \vdots & \vdots & \vdots & \ddots & \vdots \\ 0 & 0 & 0 & \cdots & \sigma_{11}^2 \end{bmatrix} \quad (18)$$

However, $\sigma_i$ (i=0, 1, etc., and 12) in the weight matrix W denotes a magnitude of variation in a measured voltage at each sense coil, for example, an ambient noise.

Moreover, the k-th $\Delta Vm$ is given by the formula (19).

$$\Delta Vm = \begin{bmatrix} Vm_0 - V_{x0}(x^{(k)}) \\ Vm_1 - V_{x1}(x^{(k)}) \\ Vm_2 - V_{x2}(x^{(k)}) \\ \vdots \\ Vm_{11} - V_{z11}(x^{(k)}) \end{bmatrix} \quad (19)$$

The position and orientation of the source coil can be calculated by proceeding with step (1) to step (4) described below.

Step (1): 0 is specified for k, and the position and orientation of the source coil are set to the initial values $(x_g, y_g, z_g)(0)$ and $(g_x, g_y, g_z)(0)$ respectively. For example, the source coil is expressed by a vector (0, 0, 1) that is oriented along the Z axis at the center position in a space in which the source coil is measured.

Step (2): the k-th matrix is calculated according to the formulas (17), (18), and (19).

Step (3): the k-th magnitude of update $\Delta x_{(k)}$ is calculated according to the formula (16).

Step (4): step (2) to step (4) are repeated until the magnitude of update $\Delta x_{(k)}$ is reduced.

In this embodiment, the sense coils oriented in the directions of the X, Y, and Z axes are arranged in order to estimate the position of the source coil. The present invention is not limited to this mode. Alternatively, the sense coils may be located at any positions and oriented in any directions. As long as the positions and orientations of the sense coils are known, the position of the sense coil can be estimated.

Operations preformed by the image processing apparatus 3 will now be described, and a description of a technique of estimating the relative shapes of an object will be provided.

Figure 10:
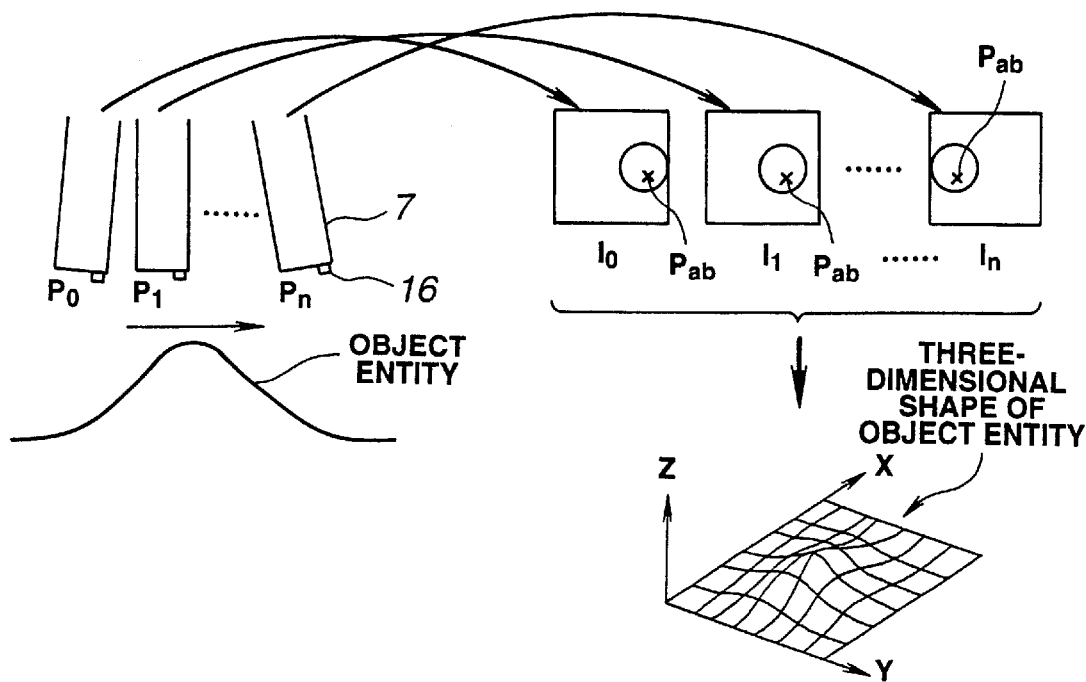

As described in the Japanese Unexamined Patent Publication No. 9-26547, images are produced by moving the imaging unit in the electronic endoscope 7. Two-dimensional image data produced time-sequentially is input to the image processing apparatus 3. As shown in FIG. 10, time-sequential images of the same object entity are produced by moving the distal part of the endoscope.

Image signals representing the object entity, which are produced by the imaging device, are processed by the video processor 11. Resultant image signals are fetched into the image processing apparatus 4. The image signals are converted into digital signals and stored as digital image data items $I_0$ to $I_n$ in the memory 51. Consequently, time-sequential images $I_0$ to In are produced in association with trajectories $P_0$ to $P_n$ made by the imaging unit.

The relative shape estimator 52 of the image processing apparatus 4 defines a plurality of points $P_{ab}$ (a=0, 1, etc, and q, b=0, 1, etc., and r) in the first image $I_0$ of the produced time-sequential images $I_0$ to $I_n$. According to a technique of template matching, the positions of points corresponding to the points $P_{ab}$ are detected in the remaining images $I_i$ (i=1, 2, etc., and n). For details of the template matching, refer to "Guide to Computer-aided Image Processing" complied under the supervision of Hideyuki Tamura (Sohken Publishing Co., Ltd., p.148–p.150).

When the positions of the corresponding points are detected in each image, displacements of the points $P_{ab}$ defined in the image $I_0$ from the corresponding points in the remaining images $I_i$ (i=1, 2, etc, and n) can be calculated. Namely, magnitudes of shifts by which the points $P_{ab}$ have shifted to the corresponding points in the images can be calculated in the form of a shift map $S_i$ (i=1, 2, etc., and n).

The shift map $S_i$ of the images $I_i$ is expressed as the magnitudes of shifts in the x and y directions as follows:

$$S_i = \begin{pmatrix} (S_{x00}, S_{y00}) & \cdots & (S_{xq0}, S_{yq0}) \\ \vdots & (S_{xab}, S_{yab}) & \vdots \\ (S_{x0r}, S_{y0r}) & \cdots & (S_{xqr}, S_{yqr}) \end{pmatrix} \quad (20)$$

A technique of color matching disclosed in the U.S. Pat. No. 4,962,540 filed by the same applicant may be adopted as a template matching technique.

Next, movements made by the imaging unit (movements made by the distal part 16 of the endoscope) will be estimated based on the shift map.

Figure 11:
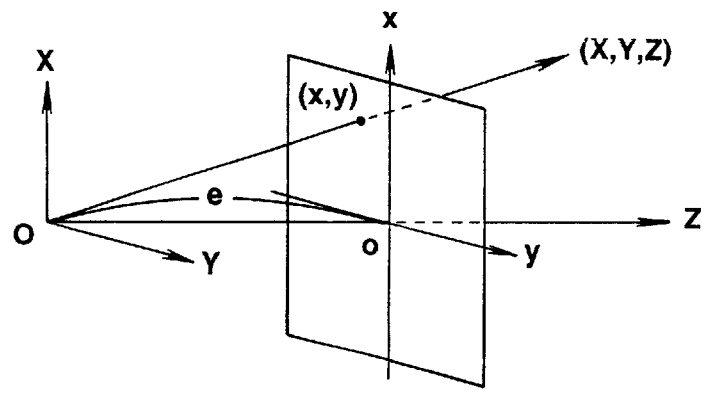

FIG. 11 shows a coordinate system for central projection. An image plane is placed perpendicularly to the Z axis at a position separated by a distance e from the origin O of an image. A point (X, Y, Z) in the space is projected as a point at which a straight line linking the point (X, Y, Z) and origin O crosses the image plane. Assuming that the coordinates of the intersection is (x, y), x and y are defined in terms of the geometric relationships as follows:

$$x = \frac{X}{Z}e \quad y = \frac{Y}{Z}e \quad (21)$$

Assume that the point X=(X, Y, Z) in the space moves to be X'=(X', Y', Z') responsive to a movement made by the imaging unit. Herein, the movement of the imaging unit is expressed, as mentioned below, using a rotational matrix R representing a rotation about a visual line passing through the origin, and a translational vector h=($h_x, h_y, h_z$).

$$X = RX' + h \quad (22)$$

The points X and X' are expressed using distances r and r' from the origin and unit directional vectors m and m' (N vector). Namely, $$X = \begin{pmatrix} X \\ Y \\ Z \end{pmatrix} = rm \quad X' = \begin{pmatrix} X' \\ Y' \\ Z' \end{pmatrix} = rm' \quad (23)$$

Herein, $$m = \frac{1}{x+y+z}\begin{pmatrix} x \\ y \\ z \end{pmatrix} \quad m' = \frac{1}{x'+y'+z'}\begin{pmatrix} x' \\ y' \\ z' \end{pmatrix} \quad (24)$$

When the formula (22) is rewritten using the formula (24), $$rm = r'Rm' + h \quad (25)$$

Figure 12A:
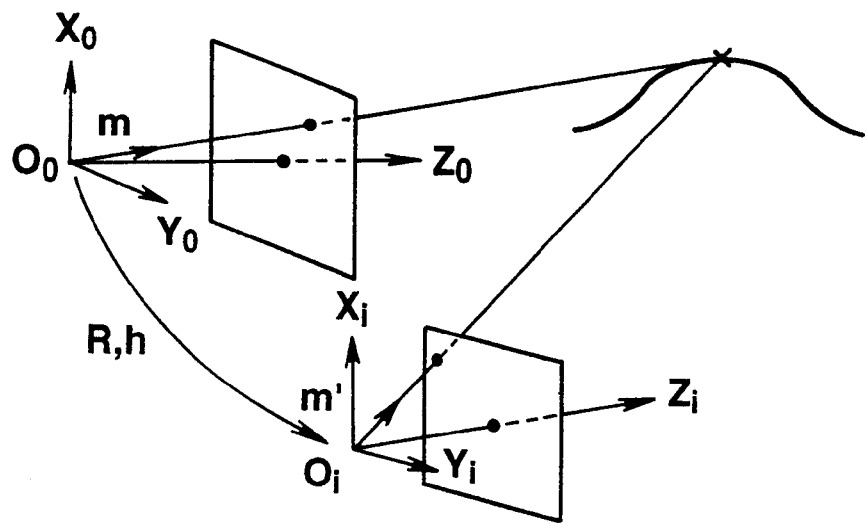
FIG. 12A is a third explanatory diagram for explaining the operations performed by the image processing apparatus shown in FIG. 6.
Figure 12B:
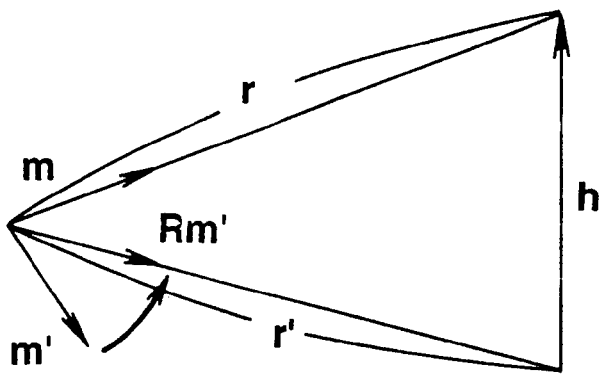
FIG. 12B is a fourth explanatory diagram for explaining the operations performed by the image processing apparatus shown in FIG. 6.

As shown in FIG. 12A and FIG. 12B, three vectors m, Rm', and h are present on the same plane in the space. The scalar triple product of the vectors is 0.

$$|mhRm'| = (m, h \times Rm') \quad (26)$$

where x indicates an outer product, and (*, *) represent an inner product.

When corresponding points in images are detected according to the template matching, there is a possibility that a shift map may contain an error stemming from a detection error. In this embodiment, the least squares method is used to estimate a rotational matrix $\hat{R}$ and translational vector $\hat{h}$ for a plurality of points set in each image. At this time, the rotational matrix $\hat{R}$ and translational vector $\hat{h}$ are estimated so that the condition expressed as the formula (27) below will be satisfied.

$$\sum_{k=1}^{M} (m_k, h \times Rm'_k)^2 \to \min \quad (27)$$

Herein, the translational vector $\hat{h}$ to be estimated is estimated as a unit vector h'.

Next, relative distances $\hat{r}$ and $\hat{r}'$ from the imaging unit to an object entity are calculated according to the estimated movements of the imaging unit.

The inner products of both the sides of the formula (25) and m and Rm' are given as follows:

$$\hat{r} = \hat{r}'(m, \hat{R}m') + (\hat{h}, m) \quad \hat{r}(m, \hat{R}m') = \hat{r}' + (\hat{h}, \hat{R}m') \quad (28)$$

The relative distances $\hat{r}$ and $\hat{r}'$ are calculated by solving the formula (28). Namely, $$\hat{r} = \frac{(\hat{h}, m) - (m, \hat{R}m')(\hat{h}, \hat{R}m')}{1 - (m, \hat{R}m')} \quad (29)$$

$$\hat{r}' = \frac{(m, \hat{R}m')(\hat{h}, m) - (\hat{h}, \hat{R}m')}{1 - (m, \hat{R}m')}$$

However, the translational vector $\hat{h}$ is estimated as the unit vector h'. The distances r and r' of the points X and X' are therefore determined with a proper magnification k as follows:

$$r = k\hat{r} \quad (30)$$

$$r' = k\hat{r}' \quad (31)$$

Consequently, relative movements ($R_i$, $h_i$ (i=1, 2, etc., and n)) are estimated based on the position of the imaging unit lay to produce the image $I_0$. The relative movements are movements made to the positions of the imaging unit lay to produce the images $I_i$ (i=1, 2, etc., and n).

The relative distances from the position, of the imaging unit lay to produce the images, to the object entity are estimated based on the relative movements estimated relative to the images $I_i$ (i=1, 2, etc., and n) and the shift map. The relative distances are equivalent to the relative shapes of the object entity visualized by the imaging unit.

The endoscopic position detecting apparatus 3 detects electromagnetic waves generated by the source coil 16 locked in the distal part of the electronic endoscope 7 according to the aforesaid method. The endoscopic position detecting apparatus 3 uses the sense coils 20k installed in the patient couch 5. The positions $P_0$ to $P_n$ of the source coil 16 in a three-dimensional space defined with the patient couch 5 as a reference are drawn out. The data of the positions is sent to the position information acquiring unit 53 of the image processing apparatus 4.

The subject shape estimator 54 of the image processing apparatus 4 stores the data of the three-dimensional positions $P_0$ to $P_n$ of the distal part of the electronic endoscope 7. The data of the three-dimensional positions $P_0$ to $P_n$ is sent from the endoscopic position detecting apparatus 3 via the position information acquiring unit 53. The three-dimensional positions at which the 0-th image data $I_0$ and n-th image data $I_n$ were produced are extracted as defined by the formula (32). The 0-th image data $I_0$ is used to estimate relative shapes.

$$P_0 = \begin{pmatrix} X_0 \\ Y_0 \\ Z_0 \end{pmatrix}, \quad P_n = \begin{pmatrix} X_n \\ Y_n \\ Z_n \end{pmatrix} \quad (32)$$

The magnitude of a shift made by the distal part of the endoscope is calculated according to the formula (33).

$$|h| = \sqrt{(X_0 - X_n)^2 + (Y_0 - Y_n)^2 + (Z_0 - Z_n)^2} \quad (33)$$

Calculated magnitudes of shifts |h| are equivalent to the magnitudes of the translational vectors h representing translations made by the camera (in this case, the distal part of the electronic endoscope). The absolute shape of the object entity can be calculated based on the magnitudes of shifts |h| and the relative shapes. As mentioned above, when relative shapes are estimated using a plurality of image data items, the translational vectors h are provided as the unit vector h' having a magnitude of 1.

A two-dimensional image depicting the estimated absolute shape seen from an appropriate observing point is then produced and displayed on the monitor 14.

The foregoing processing steps will be described in conjunction with the flowchart of FIG. 13. At step S1, the set numbers of image data items and position data items to be fetched into the image processing apparatus 4 are initialized.

At step S2, the information input unit (keyboard or the like) connected to the image processing apparatus 4 is used to input a signal which instructs whether fetching image data and position data should be started. The image data and position data are then detected.

At step S2, if it is determined that fetching the data should be started, control is passed to step S3. Otherwise, control is returned to step S1.

At step S3, the image processing apparatus 4 fetches and stores image data items $I_i$ sent from the video processor 11 and position data items $P_i$ sent from the endoscopic position detecting apparatus 3.

At step S4, i is incremented. At step S5, if termination of fetching the data is not detected, control is returned to step S3 in order to fetch image data items $I_{i+1}$ and position data items $P_{i+1}$ which are sent successively.

At step S5, if termination of fetching the data is detected, control is passed to step S6. At step S6, the relative shapes of an object entity are estimated based on the stored image data items $I_0$ to $I_n$.

At step S7, position data items $P_0$ and $P_n$ are extracted from among the stored position data items $P_0$ and $P_n$. The position data items $P_0$ and $P_n$ are associated with the 0-th image data $I_0$ and n-th image data $I_n$ which are used to estimate relative shapes. The magnitude of a shift |h| is then calculated.

At step S8, the absolute shape of the object entity is calculated based on the relative shapes estimated at step S6 and the magnitudes of shifts |h| (magnitudes of the translational vector representing translations made by the camera) calculated at step S7.

In this embodiment, the source coil 16 is passed through the forceps channel and placed in the distal part of the insertion unit 8. Alternatively, the source coil may be embedded in the distal part of the insertion unit and thus locked firmly.

In this embodiment, the main unit 19 of the endoscopic position detecting apparatus 3 and the main unit 24 of the image processing apparatus 4 are separated from each other. Alternatively, endoscopic position detecting and image processing may be carried out using a CPU and software, and may be realized by one apparatus and monitor.

As mentioned above, according to this embodiment, one source coil 16 formed with a single-core coil for generating magnetic fields is placed in the distal part of the electronic endoscope 7. Magnitudes of shifts made by the distal part can be calculated accurately, and the absolute shape of an object entity can be estimated.

The second embodiment of the invention is substantially identical to the first embodiment and therefor only a differences there between will be described. The same reference numerals will be assigned to the components identical to those of the first embodiment and any detailed description of those components will be omitted.

The configuration of the endoscopic system 1 of this embodiment include an endoscope system 2 which is unlike that of the first embodiment in that it is of a field sequential type, and the video processor 1 has a rotary filter and a sync signal output unit included in an internal light source unit thereof. The rotary filter converts white light into field sequential light. The sync signal output unit sends a sync signal synchronous with the rotary filter to the endoscopic position detecting apparatus 3. Moreover, the endoscopic detecting apparatus 3 includes a control signal producing unit which produces a control signal from the sync signal synchronous with the rotary filter which is sent from the video processor 11. The control signal is used to fetch signals generated by the sense coils 20k.

Figure 14:
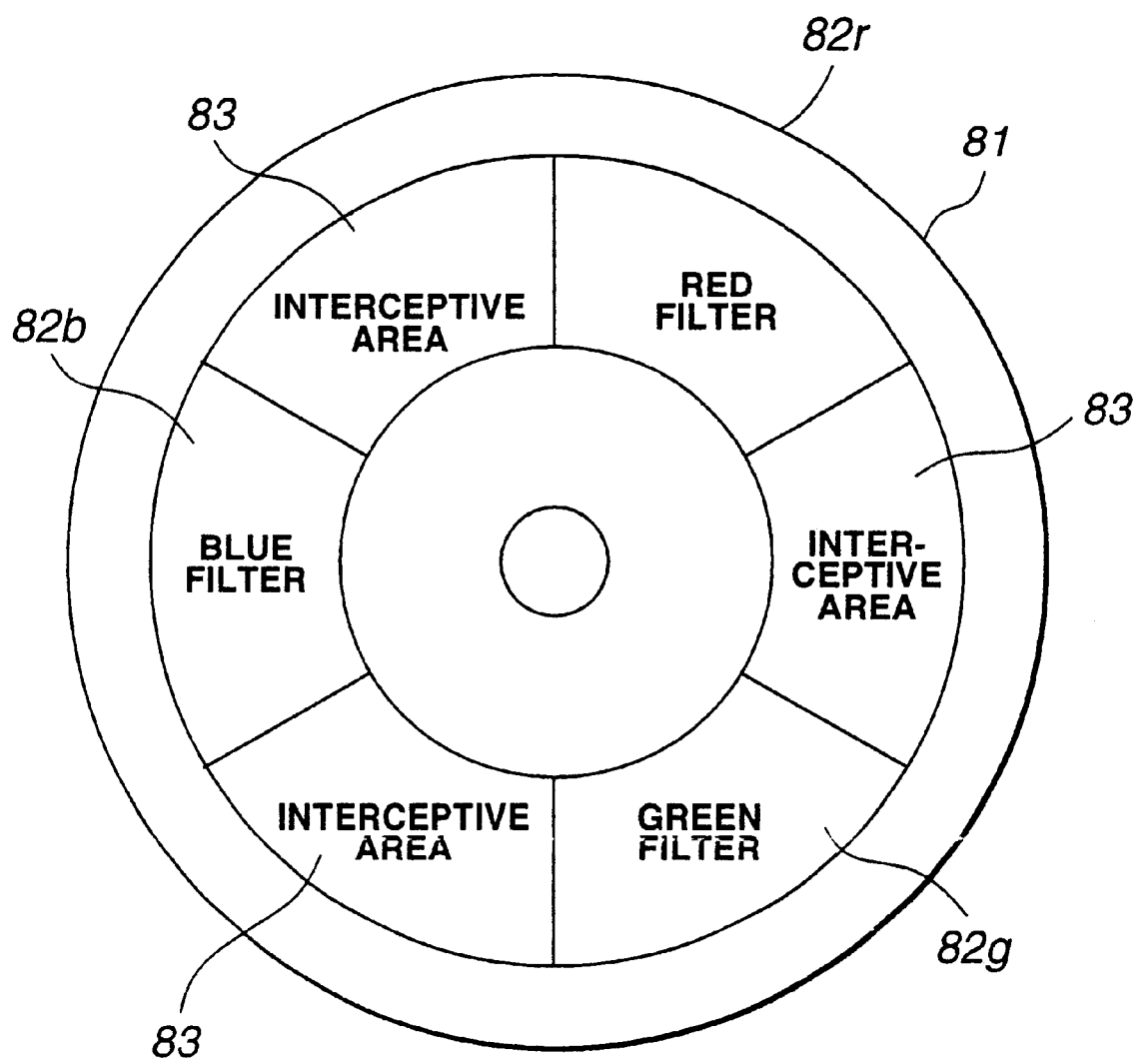

As shown in FIG. 14, a rotary filter 81 in the video processor 11 has a red filter 82r, green filter 82g, blue filter 82b arranged along the circumference thereof. The red filter 82r, green filter 82g, and blue filter 82b are transparent to light whose wavelengths fall within the spectrum of red, green, and blue radiation, respectively. An interceptive area 83 is interposed between adjoining ones of the red filter 82r, green filter 82g, and blue filter 82b of the rotary filter 81. The other components are identical to those of the first embodiment.

Light transmitted by the rotary filter 81 is irradiated on an object entity from the distal part of the electronic endoscope 7. Reflected light passes through the objective in the distal part and forms an image on the imaging device.

The imaging device accumulates charge during a period during which light is transmitted by the red filter 82r, green filter 82g, and blue filter 82b of the rotary filter 81 (hereinafter, an exposure period). The charge accumulated in the imaging device is fetched into the video processor 11 during a period during which no light is transmitted (hereinafter an interception period), and then processed and converted into an image signal.

The signal read from the imaging device is converted into digital image data items and stored in red, green, and blue memory areas.

When the red, green, and blue image data items have been stored, the video processor 11 reads the stored image data items and converts them into a standard video signal. The signal is sent to the monitor 14 and image processing apparatus 4.

Moreover, as shown in FIG. 15A to FIG. 15D, the video processor 11 generates a sync signal ($R_k$, $G_k$, $B_k$) used to sustain the rotation of the rotary filter 81. The interception and exposure periods defined by the rotary filter are repeated synchronously with the sync signal (FIG. 15A). During the interception period, charge (an image signal) is read from the imaging device (FIG. 15B). The video processor 11 sends the sync signal to the endoscopic position detecting apparatus 3 (FIG. 15C).

The main unit 19 of the endoscopic position detecting apparatus produces a control signal, which is used to detect signals generated by the sense coils 20k, from the sync signal ($R_k$, $G_k$, $B_k$). Owing to the control signal, the timing of measuring the three-dimensional position of the distal part of the electronic endoscope 7 is synchronized accurately with the timing of the imaging device producing an image. Outputs of the sense coils 20k are thus fetched (FIG. 15D). The other operations are identical to those of the first embodiment.

As mentioned above, this embodiment can provide the same advantages as the first embodiment. In addition, since image data and position data are accurately synchronized with each other, the absolute shape of an object entity can be obtained accurately.

The third embodiment of the present invention is identical to the second embodiment and, those only the differences therebetween will be described. The same reference numerals will be assigned to the components identical to those of the second embodiment and any detailed description of those components will be omitted.

The configuration of the endoscopic system 1 of this embodiment is such that an external storage device is connected to the image processing apparatus 4 as in the second embodiment of the invention. The other components are identical to those of the second embodiment.

As described in relation to the second embodiment, image data output from the video processor 11 and position data output from the main unit 19 of the endoscopic position detecting apparatus are sent mutually synchronously to the main unit 24 of the image processing apparatus.

An external storage device such as a hard disk or a digital magneto-optical disk is connected to the image processing apparatus 4. Image data and position data sent from the video processor 11 and endoscopic position detecting apparatus 3 are associated with each other and stored in the external storage device.

The image data and position data are sent mutually synchronously, and therefore stored alternately as listed in Table 1.

TABLE 1

Image data $I_0$
Position data $P_0$
Image data $I_1$
Position data $P_1$
.
.
.
Image data $I_n$
Position data $P_n$ Moreover, image data items Ii and position data items Pi (i=0, 1, 2, etc., and n) necessary to estimate an absolute shape are stored in the image processing apparatus 4. The stored data items are stored in respective areas as listed in Table 2.

TABLE 2

Image data $I_0$
Image data $I_1$
.
.
.
Image data $I_n$
Position data $P_0$
Position data $P_1$
.
.
.
Position data $P_n$ The image processing apparatus 4 reads data from the external storage device, and stores it in the memory 51. The image processing apparatus 4 executes the processing steps succeeding step S6 in FIG. 13, which have been referred to in relation to the first embodiment, and thus estimates the absolute shape of an object entity.

A two-dimensional image is produced to depict the estimated absolute shape seen from an appropriate observing position, and then displayed on the monitor 14.

Moreover, as mentioned in relation to the first embodiment, the video processor 11 and endoscopic position detecting apparatus 3 may not be synchronized with each other accurately. In this case, time instants $t_{Ia}$ (a=0, 1, 2, etc., and n) and time instants $t_{Ib}$ (b=0, 1, 2, etc., and m) are, as listed in Table 3, stored in the external storage device in association with image data items $I_a$ (a=0, 1, 2, etc., and n) or position data items $P_b$ (b=0, 1, 2, etc., and m). The time instants $t_{Ia}$ are time instants at which an image signal is read from the imaging device after the image processing apparatus 4 executes processing. The time instants $t_{Ii}$ are time instants at which voltages at the sense coils are detected.

TABLE 3

| Image data $I_0$ | $t_{I0}$ |
|---|---|
| Image data $I_1$ | $t_{I1}$ |
| Position data $P_0$ | $t_{P0}$ |
| Image data $I_2$ | $t_{I2}$ |
| Image data $I_3$ | $t_{I3}$ |
| Position data $P_1$ | $t_{P1}$ |
| . | . |
| . | . |
| . | . |
| Image data $I_{n-1}$ | $t_{In-1}$ |
| Image data $I_n$ | $t_{In}$ |
| Position data $P_m$ | $t_{Pm}$ |

The image processing apparatus 4 reads image data and position data and their relevant information from the external storage device, stores them in the memory 51, and estimates an absolute shape.

Since the stored image data and position data are not mutually synchronous, positions at which the image data items were produced by the imaging device are inconsistent with the position data items. The positions at which the image data items were produced must be estimated based on the stored position data items.

Position data items of positions preceding and succeeding the positions at which the image data items $I_i$ were produced are defined as follows:

$$P_j = \begin{pmatrix} x_j \\ y_j \\ z_j \end{pmatrix}, \quad P_{j+1} = \begin{pmatrix} x_{j+1} \\ y_{j+1} \\ z_{j+1} \end{pmatrix} \quad (34)$$

The preceding and succeeding positions $P_j$ and $P_{j+1}$ are weighted according to the time instants $t_{Ii}$, at which the image data items $I_i$ were produced, and the time instants $t_{Pj}$ and $t_{Pj+1}$ at which the position data items were detected. The positions $P_{Ii}$ at which the image data items $I_i$ were produced are estimated according to the formula (35) below.

$$P_{I_i} = \alpha P_j + (1 - \alpha) P_{j+1} \quad (35)$$

$$\alpha = \frac{t_{P_{j+1}} - t_{I_i}}{t_{P_{j+1}} - t_{P_j}}$$

$$P_{I_i} = \begin{pmatrix} x_{I_i} \\ y_{I_i} \\ z_{I_i} \end{pmatrix} = \alpha \begin{pmatrix} x_j \\ y_j \\ z_j \end{pmatrix} + (1 - \alpha) \begin{pmatrix} x_{j+1} \\ y_{j+1} \\ z_{j+1} \end{pmatrix}$$

Herein, the positions at which image data items were produced are estimated by performing linear weighting and addition. Alternatively, position data items preceding and succeeding the positions at which the imaging device produced image data may be nonlinearly weighted and then added up.

As mentioned above, this embodiment provides the same advantages as the second embodiment of the invention. In addition, image data sent from the video processor 11 and position data sent from the endoscopic position detecting apparatus 3 are stored while associated with each other. An object entity can be measured at any required time instant.

Moreover, as described in relation to the first embodiment, the video processor 11 and endoscopic position detecting apparatus 3 may not be synchronized with each other. Nevertheless, the positions at which the imaging device produced images can be predicted based on the stored position data. This is because the data items concerning the timing of fetching position data and the timing of fetching image data are stored concurrently.

In the present invention, it is apparent that a wide range of different embodiments can be constructed based on the invention without a departure from the spirit and scope of the invention. This invention is limited by the appended claims but not restricted by any specific embodiments.

What is claimed is:

1. An endoscopic image processing system, comprising:
   an imaging device which produces endoscopic images of a subject through an objective;
   an image memory which stores a plurality of images produced by the imaging device;
   a relative shape estimator which estimates relative shapes depicted by the plurality of images according to image signals representing the plurality of images stored in the memory;
   a first coil located near the objective;
   a position information detector, having a second coil disposed at a predetermined position, which detects the positions of the first coil by utilizing magnetic fields;
   a position information acquiring unit which obtains position information of the positions detected by the position information detector in association with the respective images stored in the image information memory; and
   a subject shape estimator which estimates the shape of the subject according to the relative shape information of the relative shapes estimated by the relative shape estimator and the position information acquired by the position information acquiring unit.

2. An endoscopic image processing system, comprising:
   an endoscope having an insertion unit provided with a distal part and a bending portion capable of being angled;
   an objective located in the distal part of the insertion unit;
   an imaging unit which obtains an image of a subject through the objective;
   an image memory which stores a plurality of endoscopic images produced by the imaging unit;
   a relative shape estimator which estimates relative shapes depicted by the plurality of endoscopic images according to image signals representing the plurality of endoscopic images stored in the image memory;
   a first coil located in the distal part of the insertion unit;
   a position information detector, having a second coil disposed at a predetermined position, which detects the positions of the first coil by utilizing magnetic fields;
   a position information acquiring unit which obtains position information of the positions detected by the position information detector in association with the respective endoscopic images stored in the image information memory; and
   a subject shape estimator which estimates the shape of the subject according to the relative shape information of the relative shapes estimated by the relative shape estimator and the position information acquired by the position information acquiring unit.

3. A shape estimating method, comprising the steps of:
   producing subject images through an objective using an imaging unit;

storing a plurality of subject images produced by the imaging unit;

estimating relative shapes depicted by the plurality of subject images according to image signals representing the plurality of stored subject images;

detecting the positions of a first coil located near the objective using magnetic fields by way of a position information detector having a second coil disposed at a predetermined position;

acquiring position information of the detected positions in association with the respective stored subject images; and estimating the shape of the subject according to the relative shape information of the estimated relative shapes and the acquired position information.

4. An endoscopic image processing system, comprising:

an endoscope having an imaging device which images an object entity at different positions;

a relative shape estimator which estimates relative shapes of the object entity using a plurality of images produced by the imaging device;

a position detector which detects positions in a three-dimensional space of a distal part of the endoscope by utilizing a coil; and an estimator which estimates an absolute shape of the object entity according to the relative shapes of the estimated object entity and the output of the position detector.

5. An endoscopic image processing system according to claim 4, wherein the position detector includes a source coil which generates magnetic fields and is disposed in the distal part of the endoscope; and a plurality of sense coils which detect magnetic fields generated by the source oil, the sense coils being arranged in a three-dimensional space, the position detector being operable to detect the positions in three-dimensional space of the source coil according to the outputs of the sense coils.

6. An endoscopic image processing apparatus according to claim 5, wherein the source coil is a single-core coil.

7. An endoscopic image processing apparatus according to claim 5, wherein the sense coils are single-core coils.

8. An endoscopic image processing apparatus according to claim 5, wherein the sense coils are triaxial coils.

9. An endoscopic image processing system according to claim 4, wherein the position detector includes a plurality of source coils which generate magnetic fields and are arranged in the three-dimensional space; and a sense coil which detects the magnetic fields generated by the source coils and is disposed in the distal part of the endoscope, the position detector being operable to detect the positions in the three-dimensional space of the sense coil according to the output of the sense coil.

10. An endoscopic image processing apparatus according to claim 9, wherein the source coils are single-core coils.

11. An endoscopic image processing apparatus according to claim 9, wherein the sense coil is a single-core coil.

12. An endoscopic image processing apparatus according to claim 9, wherein the sense coil is a triaxial coil.

13. An endoscopic image processing apparatus according to claim 4, further comprising a synchronizing unit which synchronizes timing of the position detector performing its function of detecting a position with the timing of the imaging unit performing its function of imaging an object entity.

14. An endoscopic image processing apparatus according to claim 4, further comprising a two-dimensional image producing unit which depicts the absolute shape of the object entity observed at any observation point.

15. An endoscopic image processing apparatus according to claim 4, further comprising a memory which stores a plurality of images produced by the imaging unit and the information of the positions of the distal part of the endoscope detected by the position detector.

16. An endoscopic image processing apparatus according to claim 15, wherein time instants at which the imaging unit produces endoscopic images, and time instants at which the position detector detects the positions of the distal part of the endoscope are stored in the memory in association with the image or position data items.

17. An endoscopic image processing apparatus according to claim 16, wherein the position detector includes a position estimator which estimates the positions at which the distal part of the endoscope are located: (i) at the time instants at which the imaging unit produces the images; (ii) according to the positions of the distal part of the endoscope stored in the memory; (iii) the time instants at which the position detector detects the positions of the distal part of the endoscopic; and (iv) the time instants at which the imaging unit produces the endoscopic images.

18. An endoscopic image processing apparatus according to claim 17, wherein the position estimator includes an interpolating unit which calculates the positions of the distal part of the endoscope at time instants by performing interpolation according to the plurality of positions of the distal part of the endoscope and the detected time instants which are stored in the memory; and the positions of the distal part of the endoscope are estimated according to the time instant at which the endoscopic images are produced and stored in the memory, and the output of the interpolating unit.

* * * * *